United States Patent
Nigam et al.

(10) Patent No.: US 6,480,739 B1
(45) Date of Patent: Nov. 12, 2002

(54) AVOIDING FAR-FIELD QRS IN A TACHY DETECTIONS DEVICE

(75) Inventors: Indra B. Nigam, Tigard, OR (US); Andreas Hahn, Berlin (DE); Andreas Kucher, Schwedt (DE); Mrigank Shekhar, Tualatin, OR (US)

(73) Assignee: Biotronik Mess - und Therapiegeräte GmbH & Co. Ingenieurbüro Berlin, Berlin (DE)

( * ) Notice: Subject to any disclaimer, the term of this patent is extended or adjusted under 35 U.S.C. 154(b) by 0 days.

(21) Appl. No.: 09/701,796

(22) PCT Filed: Apr. 10, 2000

(86) PCT No.: PCT/EP00/03174
§ 371 (c)(1),
(2), (4) Date: Mar. 30, 2001

(87) PCT Pub. No.: WO00/61225
PCT Pub. Date: Oct. 19, 2000

Related U.S. Application Data

(63) Continuation of application No. 09/288,235, filed on Apr. 8, 1999, now abandoned.

(51) Int. Cl.$^7$ ............................................. A61N 1/362
(52) U.S. Cl. ............................. 607/9; 607/14; 600/509
(58) Field of Search ............................. 607/27, 9, 14; 600/509, 521; 128/901, 902

(56) References Cited

U.S. PATENT DOCUMENTS

| | | | |
|---|---|---|---|
| 5,735,881 A | 4/1998 | Routh et al. | |
| 5,755,739 A | 5/1998 | Sun et al. | |
| 5,759,196 A | 6/1998 | Hess et al. | |
| 6,058,327 A | * 5/2000 | Borgerding et al. | 607/9 |

FOREIGN PATENT DOCUMENTS

EP        0 705 620 A2    10/1996

* cited by examiner

*Primary Examiner*—Kennedy Schaetzle
(74) *Attorney, Agent, or Firm*—Venable; Robert Kinberg

(57) ABSTRACT

Method for avoiding the detection of a far-field QRS by the atrial detector of a heart pacemaker or ICD while allowing the detection of a true atrial signal to a maximum possible extent; the method comprising generating a Short Atrial Refractory Period (SARP) following an atrial sensed or paced event by means of a SARP timer, blanking of the atrial detector following a ventricular paced event, generating a Post Ventricular Short Atrial Refractory Period (PVSARP) following a ventricular sensed or paced event by means of a PVSARP timer, generating a temporary decrease in the sensivity of an amplifier for the atrial signal for a time period following the elapse of the mentioned PVSARP, and gradually increasing the sensitivity of the amplifier for the atrial signal after said time period.

8 Claims, 2 Drawing Sheets

AVOIDING FAR-FIELD QRS IN A TACHY DETECTIONS DEVICE

CROSS-REFERENCE TO RELATED APPLICATION

This U.S. National Stage application is a Continuation of U.S. application Ser. No. 09/288,235 filed Apr. 8, 1999, now abandoned, the subject matter of which is incorporated herein by reference.

BACKGROUND OF THE INVENTION

In a dual-chamber cardiac pulse generator, it is desirable not to detect a far-field QRS Signal and mistake it for being a P-wave. In a bradycardia pacemaker where detection of high atrial rate is not necessary, this is avoided by keeping the atrial detector refractory during periods where far-field QRS or other unwanted signals might be present. One example of such an atrial refractory period is the so called "Total Atrial Refractory Period" (TARP) which starts at an atrial event and, by having an appropriate value, remains in effect until a reasonable amount of time after the following ventricular event. Another example is keeping the atrial detector refractory until the following ventricular event and then starting a "Post Ventricular Atrial Refractory Period" (PVARP) having a reasonable duration. However, in devices where detection of high atrial rate is necessary, examples being ICDs and also pacemakers implementing mode switching as a result of high atrial rate, the mentioned TARP and PVARP may result in undersensing of a true atrial signal, thereby compromising the response from the device. It can be mentioned here that the purpose of the PVARP (or the portion of the TARP that remains after a ventricular sensed or paced event) is to prevent initiation of the so called Pacemaker Mediated Tachycardia (PMT) by avoiding sensing of the retrograde conduction by the atrial detector (which in an atrial tracking mode would lead to triggering of a ventricular pacing pulse).

SUMMARY OF THE INVENTION

The invention allows use of short atrial refractory periods when attempting to detect high atrial rate (if prevailing).

A scheme aimed at detecting maximum possible amount of true atrial signal while avoiding far-field QRS and other unwanted signal is disclosed. The innovation lies in the avoidance of the far-field QRS. Other unwanted signals, e.g. other parts than the P-wave of the atrial signal, can be handled by an appropriate atrial refractory period which need not be very long, thus allowing detection of a high true atrial rate.

Thereby a mechanism is implemented, so that the shortest possible Short Atrial Refractory Period (SARP) and Post Ventricular Short Atrial Refractory Period (PVSARP) can be used, thus enabling detection of high rate atrial rhythms.

DETAILED DESCRIPTION OF THE INVENTION

Figure 1:
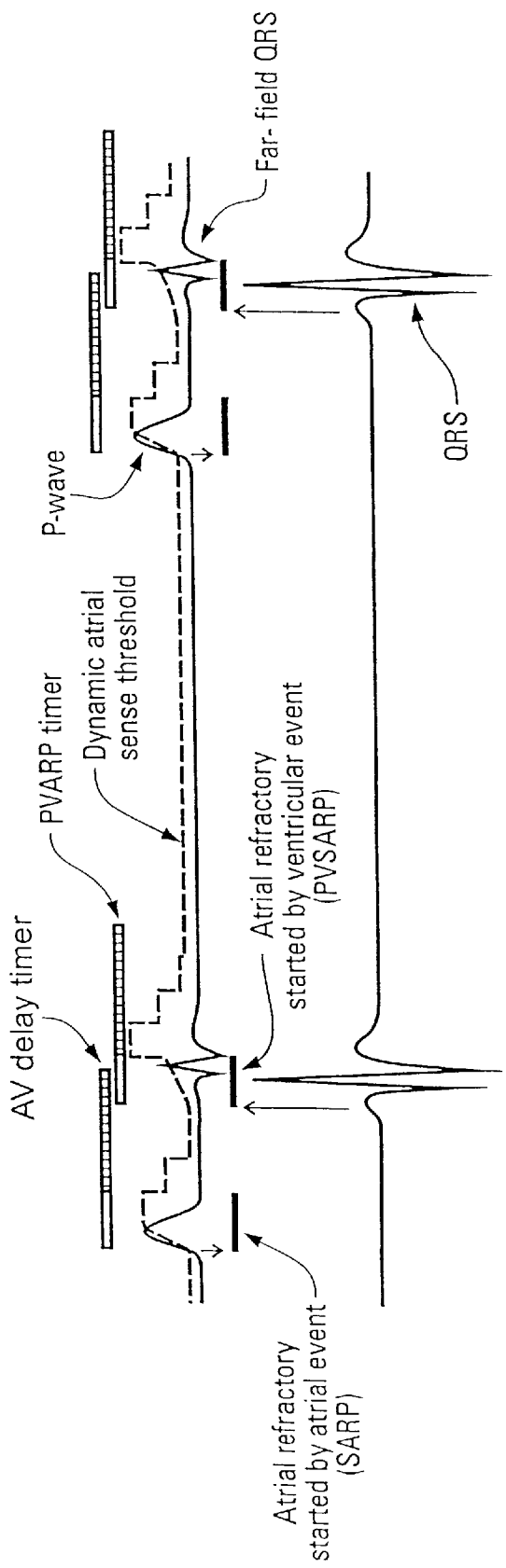
FIG. 1 shows a "Short Atrial Refractory Period" (SARP) following an atrial sensed or paced event. The SARP is as short as possible, but long enough to avoid multiple sensing and detection of unwanted artifacts of the atrial signal.

Please refer to FIG. 1 for the following description. The present invention suggests use of a "Post Ventricular Short Atrial Refractory Period" (PVSARP) following a ventricular sensed event. Following the elapse of the mentioned PVSARP, the invention further suggests temporarily decreasing the sensitivity of the atrial detector and increasing gradually the sensitivity to its normal value. The temporary decrease in the sensitivity helps in keeping the PVSARP very short, thus leading to detection of a true atrial signal to the maximum possible extent. The value of the PVSARP must be determined individually for each patient by monitoring the signal and the response of the atrial detector. One value of the PVSARP could be zero.

A further improvement is suggested by determining the amount of temporary decrease in the atrial sensitivity as a function of its current value (i.e. the sensitivity in effect before enforcing the decrease). Yet another improvement is suggested by determining the amount of the temporary decrease in atrial sensitivity as a function of a value acquired by letting the dynamic sensitivity threshold reach the peak of an input signal—as seen during the PVSARP—towards the end of the PVSARP. The PVSARP and the temporary decrease in the atrial sensitivity are aimed at avoiding sensing the far-field QRS signal by the atrial detector.

While the use of a short SARP and a short PVSARP helps in detecting high atrial rate, for the traditional bradycardia support function in the same device, the invention further suggests incorporation of an AV delay timer and PVARP timer as shown in FIG. 1. While these timers are running, the atrial detector must be kept logically refractory as far as the bradycardia support is concerned—what this means is that the bradycardia timings etc. must not be affected by any atrial detections which may occur while any of these two timers is running. Please note that atrial detections are possible only in the zone shown with crosshatches since the atrial detector is refractory due to SARP or PVSARP initially (the zone shown in clear). Also note that the figure illustrates a running AV delay timer determined by a ventricular sensed event. In devices based on the use of a TARP, a TARP timer can be implemented instead of an AV delay and PVARP timers.

Following a ventricular paced event, the atrial detector is blanked for some time to avoid detection of the ventricular pacing pulse or its after-potential by the atrial detector and also to avoid saturation of the atrial detector. The disclosed scheme can be used, together with blanking the atrial detector, also following a ventricular paced event.

Figure 2:
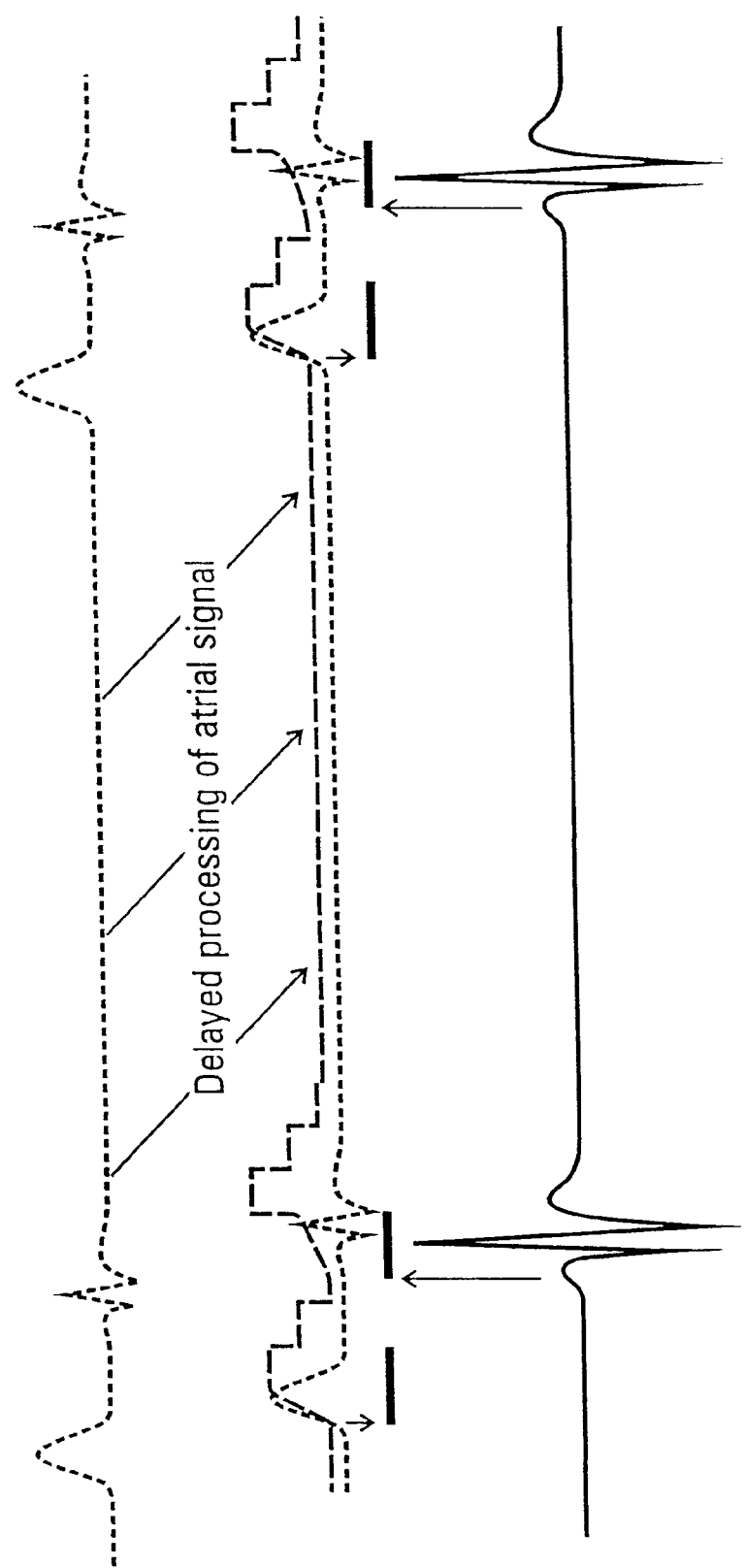
FIG. 2 illustrates delayed processing of an atrial signal.

In rare cases, a QRS may be "seen" by the atrial detector before it is sensed by the ventricular detector. The invention advocates a delayed signal processing by the atrial detector to manage such cases. The top trace in FIG. 2 is the input signal to the atrial detector; the middle trace (shown using a dotted line) is the delayed signal. It has been found that this delay need not be very long (16 ms is usually enough). This delay will automatically discard the "seen" early QRS as soon as the QRS is sensed by the ventricular detector resulting in the start of the PVSARP.

What is claimed is:

1. A method for avoiding detection of a far-field QRS by an atrial detector of a heart pacemaker or ICD while allowing detection of a true atrial signal to the maximum possible extent, comprising the steps of:

generating a Short Atrial Refractory Period (SARP) following an atrial sensed or paced event by means of a SARP timer;

blanking the atrial detector following a ventricular paced event;

generating a Post Ventricular Short Atrial Refractory Period (PVSARP) following a ventricular sensed or paced event by means of a PVSARP timer;

generating a temporary decrease in atrial sensitivity of an amplifier for the atrial signal for a time period following the elapse of the mentioned PVSARP; and gradually increasing the sensitivity of the amplifer for the atrial signal after said time period.

2. The method according to claim 1, further comprising the steps of:

starting, for a bradycardia support function, an AV-delay timer following an atrial sensed or paced event or following the elapse of the SARP; and starting a Post Ventricular Atrial Refractory Period (PVARP) timer following a ventricular sensed or paced event following the elapse of the PVSARP; the bradycardia support remaining unaffected by atrial detections which occur while any of these two timers is running.

3. The method according to claim 1 further comprising the step of:

starting, for bradycardia support function, a Total Atrial Refractory Period (TARP) timer following an atrial sensed or paced event or following the elapse of the SARP, the bradycardia support remaining unaffected by atrial detections which occur while this timer is running.

4. The method according to claim 1, wherein the step of generating the PVSARP includes selecting the duration of the PVSARP to be zero.

5. The method according to claim 1, wherein the step of generating a temporary decrease in atrial sensitivity includes decreasing the sensitivity by an amount which is a function of its current dynamic value.

6. The method according to claim 5, wherein the step of generating a temporary decrease in atrial sensitivity includes setting an atrial sensitivity threshold to the peak of the input signal—as found during the PVSARP—towards the end of the PVSARP; and decreasing the atrial sensitivity by an amount based on this value.

7. The method according to claim 1, wherein the step of generating a temporary decrease in atrial sensitivity includes selecting the temporary decrease in atrial sensivity so as to bring the sensitivity to a fixed level.

8. The method according to claim 1, further comprising the steps of:

delayed processing of the signal by the atrial detector to avoid detection of a far-field QRS which precedes the detection by a ventricular detector; and automatically discarding at the start of a PVSARP a signal which may be waiting to be processed.

* * * * *